United States Patent [19]

Einck

[11] Patent Number: 5,763,417
[45] Date of Patent: Jun. 9, 1998

[54] PROTECTION FROM SEPTIC SHOCK SUBSEQUENT TO INJURY BY DSRNAS

[75] Inventor: Leo Einck, McLean, Va.

[73] Assignee: Hemispherx Biopharma, Inc., Philadelphia, Pa.

[21] Appl. No.: 469,625

[22] Filed: Jun. 6, 1995

Related U.S. Application Data

[63] Continuation of Ser. No. 216,518, Mar. 23, 1994, abandoned, which is a continuation of Ser. No. 44,880, Apr. 9, 1993, abandoned, which is a continuation of Ser. No. 831,743, Feb. 10, 1992, abandoned, which is a continuation of Ser. No. 713,001, Jun. 10, 1991, abandoned, which is a continuation of Ser. No. 574,524, Aug. 28, 1990, abandoned, which is a continuation of Ser. No. 419,663, Oct. 11, 1989, abandoned.

[51] Int. Cl.$^6$ ............................................. A61K 31/70
[52] U.S. Cl. .............................. 514/44; 514/885; 514/921
[58] Field of Search ................................. 514/44, 885, 921

[56] References Cited

U.S. PATENT DOCUMENTS

| | | | |
|---|---|---|---|
| 4,795,744 | 1/1989 | Carter | 514/44 |
| 4,945,082 | 7/1990 | Carter | 514/44 |
| 4,963,532 | 10/1990 | Carter | 514/44 |

FOREIGN PATENT DOCUMENTS

| | | | |
|---|---|---|---|
| 0213921 | 8/1986 | European Pat. Off. | 514/44 |
| 0 299 745 | 1/1989 | European Pat. Off. | |
| 0 300 680 A3 | 1/1989 | European Pat. Off. | |
| 0 306 347 | 3/1989 | European Pat. Off. | |
| 0 308 066 A3 | 3/1989 | European Pat. Off. | |
| 2046506 | 9/1970 | Germany | 514/44 |
| 1916332 | 10/1970 | Germany | 514/44 |

OTHER PUBLICATIONS

Surgical Forum, vol. 40, 1989, pp. 95–97 Jones et al "Restoration of delayed–type hypersensitivity . . . injury".
The Lancet, vol. 1, No. 8545, Jun. 1987 pp. 1286–1292 Carter et al "Clinical, immunological and virological . . . AIDS–related complex".
Biological Abstract #85341 (Zapata et al) 1986. vol. 81(9).
Biological Abstract #73790 (Sharma et al) 1981. vol. 72 (11).

*Primary Examiner*—James O. Wilson
*Attorney, Agent, or Firm*—Nixon & Vanderhye PC

[57] ABSTRACT

The use of dsRNA for use in the reactivation of natural defense systems within human cells, tissues and organs reduced to inadequate function subsequent to injury. Specific treatments for various clinical phases of the biological continuous of an acquired immune deficient state are described. Protection from the toxic effects associated with increased TNF levels is described.

3 Claims, No Drawings

PROTECTION FROM SEPTIC SHOCK SUBSEQUENT TO INJURY BY DSRNAS

CROSS-REFERENCES TO RELATED APPLICATIONS

This is a Rule 62 File Wrapper Continuation of application Ser. No. 08/216,518, filed Mar. 23, 1994, now abandoned, which is a continuation of application Ser. No. 08/044,880, filed Apr. 9, 1993, now abandoned, which is a continuation of application Ser. No. 07/831,743, filed Feb. 10, 1992, now abandoned, which is a continuation of application Ser. No. 07/713,001, filed Jun. 10, 1991, now abandoned, which is a continuation of application Ser. No. 07/574,524, filed Aug. 28, 1990, now abandoned, which is a continuation of application Ser. No. 07/419,663, filed Oct. 11, 1989, now abandoned.

BACKGROUND OF THE INVENTION

Field of Invention

Discussion of the Relevant Prior Art

Impaired immunologic reactivity following shock or injury is well documented. Using a variety of measurements of immunological status following a wide range of types of surgical procedure or injury, a pattern of immune dysfunction can be identified[1]. The immune dysfunction begins within hours of injury and continues for days or weeks depending upon the severity of injury and the patient. Failure of the immune system to recover function correlates with increased morbidity (sepsis) and mortality[2]. For example, it has been reported that the impaired immunological reactivity following major surgery is a central, underlying cause of the susceptibility of the injured individual to opportunistic infections[3]. This susceptibility manifests itself in complications such as sepsis, delayed wound healing, abscesses, and adult respiratory distress syndrome (ARDS), sometimes referred to as multiple organ failure.

[1]Meakins J. L., Pietsch J. B., Bubenick O., Kelley R., Rode H., Gordon J. and MacLean L. D., Delayed Hypersensitivity: Indicator of acquired failure of host defenses in sepsis and trauma, Ann Surg 1977, 186:241–246.

[2]Tellado-Rodriguez, J. and Christou, N. V. Clinical Assessment of Host Defense, Surgical Clinics of North America February 1988, 68(1)41–55.

[3]Faist E., Ertel W., Salmen B., Weiler A., Ressel C., Bolla K. Heberer G., The immune-enhancing effect of perioperative thymopentin administration in elderly patients undergoing major surgery, Arch Surg December 1988, 123:1449–1453.

This acquired immune deficient state is brought about by a wide range of insults including trauma, burns, surgery, transfusion, radiation therapy and some chemotherapy. This syndrome manifests itself as the disease state whereby a complete and functional immune system is rendered ineffectual in a relatively short time. The short interval between insult and immune dysfunction suggests that the immune deficient is brought about by changes in cytokine levels[4]. Cytokines are molecules which are released by cells into the blood to modulate the activity of other component cells of the immune system. Changes in cytokine levels correlate with observed changes in the activity levels of the immune system. However, the mechanism by which the immune system is controlled is very poorly understood. The interactions of the currently identified cytokines are the subject of intense research and speculation. Certainly additional cytokines will be identified in the future.

[4]MacPhee M., Christou N. V., Gordon J., Chartrand L., Rode H., Quantitative and qualitative study of the restoration by cytokines of mononuclear cell delivery to skin test sites in anergic surgical patients, Arch Surg December 1988, 123:1470–1473.

Some individual cellular components of the immune system and their apparent functions are beginning to be established. A variety of methods of quantitating immune activity and function are known. The proliferation rate of lymphocytes following stimulation, the migration rate of macrophages, the rate of phagocytosis of macrophages, antibody production by B-lymphocytes, and many other tests are available. Notable for its simplicity and reproducibility is the skin test (delayed type hypersensitivity, or DTH), where antigens are introduced subdermally and the response of the cell-mediated immune system is measured by induration (swelling) of the subdermal layer of the skin. A positive skin test represents the summation of a host of immune competent cells effecting a cascade of individual events in response to a perceived foreign antigen. DTH therefore tests the sum responsiveness of the components of the entire immune system.

Macrophages represent a particularly significant component of the immune system in burn injury and trauma as the macrophages are the immune cells which migrate to the injury site and engulf bacterial cells as they invade the wound site. Macrophages therefore replace the skin within the injury as the first line of defense against infection. Macrophage activity can be assayed by examining the rate of phagocytosis (the engulfing process) by determining the cellular uptake of latex beads by macrophages.

Immune incompetence following burn trauma is well-recognized. One aspect of the host defense network which appears to be especially sensitive to the effects of trauma is cell-mediated immunity. Although cell-mediated immunity is a very complex process involving many cell types, the overall status of this immunologic response can easily and reliably be assessed by testing the delayed hypersensitivity skin reaction to injected antigen. Following thermal injury, the skin test becomes less reactive, that is, the size of the area of induration (swelling) 48 hours after antigen injection becomes smaller than usual. Patients that show a subsequent increase in skin test reactivity, and thereby demonstrate partial restoration of cell-mediated immunity, have an improved prognosis[5]. Further, the rate of recovery of immune function (as assayed by skin test reactivity) can be correlated with survival[6].

[5]Hiebert J. M., McGough M., Rodeheaver G., Tobiasen J., Edgerton M. T., Edlich R. F., The influence of catabolism on immunocompetence in burned patients, Surgery August 1979 86(2):242–247.

[6]Kagan R. J., Bratescu A., Jonasson O., Matsuda T., Teodorescu M., The relationship between the percentage of circulating B cells, corticosteroid levels, and other immunologic parameters in thermally injured patients, J Trauma 1989 February; 29(2):208–13.

Other indicators of immune function are also depressed in thermally injured patients. These include T cell numbers[7], HLA-DR antigens[8], B-cell numbers[9], leukocyte function[10], compliment function[11], depressed lymphoproliferative responses[12], graft verses host (GVH) response[13], and heterophil chemotaxis[14]. The immunological sequela following thermal injury have been reviewed[15]. In addition, changes in some cytokine levels have been characterized subsequent to thermal injury[16].

[7]Calvano S. E., deRiesthal H. P., Marano M. A., Antonacci A. C., The decrease in peripheral blood CD4+ T cells following thermal injury in humans can be accounted for by a concomitant decrease in suppressor-inducer CD4+ T cells as assessed using anti-CD45R, Clin Immunol Immunopathol 1988 May; 47(2):164–73.

[8]Gibbons R. A., Martinez O. M., Lim R. C., Horn J. K., Garovoy M. R., Reduction in HLA-DR, HLA-DQ and HLA-DP expression by Leu-M3+ cells from the peripheral blood of patients with thermal injury, Clin Exp Immunol 1989 March; 75(3):371–5.

[9]Kagan R. J., Bratescu A., Jonasson O., Matsuda T., Teodorescu M., The relationship between the percentage of circulating B cells, corticosteroid levels, and other immunologic parameters in thermally injured patients, J Trauma 1989 February; 29(2):208–13.

[10]Tchervenkov J. I., Latter D. A., Psychogios J., Christou N. V., Altered leukocyte delivery to specific and nonspecific inflammatory skin lesions following burn injury, J Trauma 1988 May; 28(5):582-8.
[11]Bjornson A. B., Bjornson H. S., Lincoln N. A., Altemeier W. A., Relative role of burn injury, wound colonization and wound infection in induction of alterations of complement function in a guinea pig model of burn injury, J. Trauma 1984 24:106–115.
[12]Singh H., Herdon D. N., Stein M. D., Kinetics of lymphoproliferativ responses following scald injury in a rat burn model, Clin Immuno and Immunopath 1986 40:476–484.
[13]Shelby J., Merrell S. W., In vivo monitoring of postburn immune response, J. Trauma 1987 27:213–216.
[14]Davis J. M., Gallin J. I., Abnormal rabbit heterophil chemotaxis following thermal injury, Arch Surg 1988 June 123:752–755.
[15]Winkelstein A., What are the immunological alterations induced by burn injury? J. Trauma 1984 September 24(9):S72–S83. What is the relationship between the status of a patient's host defense mechanisms, his metabolic response and his ability to respond to injury? J. Trauma 1984 September 24(9): S84–S100.
[16]Antonacci A. C., How do immunomodulators affect host defense in the burn patient? J. Trauma 1984 September 24(9):S101–S118.

A number of immunomodulating drugs have been tested for efficacy in restoring acquired immune dysfunction. Ibuprofen and Interleukin 2[17], recombinant human granulocyte colony-stimulating factor (rhGCSF)[18]. Prostaglandin E[19], RU 41740 (Biostim)[20], Levamisole[21] and Thymopentin[22] have been identified as potential therapeutic agents. These drugs are in animal studies or early clinical trials to determine if they are efficacious. Preliminary results would indicate that they have efficacy in a limited number of individuals and are usually not effective unless administered prior to injury. This limits the clinical utility of these potential therapies.

[17]Shelby J., Hisatake G., Effect of ibuprofen and interleukin 2 on transfusion-induced suppression of cell-mediated immunity, Arch Surg 1988 November 123:1397–1399.
[18]Mooney D. P., Gamelli R. L., O'Reilly M., Herbert J. C., Recombinant human granulocyte colony-stimulating factor and Pseudomonas burn wound sepsis, Arch Surg 1988 September 123:1353–1357.
[19]Waymack J. P., Yurt R. W., Effect of prostaglandin E on immune function in multiple animal models, Arch Surg 1988 November 123:1429–1432.
[20]Christou N. V., Zakaluzny I., Marshall J. C., Nohr C. W., The effect of the immunomodulator RU 41740 (Biostim) on the specific and nonspecific immunosupression induced by thermal injury or protein deprivation, Arch Surg 1988 February 123:207–211.
[21]Meakins J. L., Christou N. V., Shizgal H. M., MacLean L. D., Therapeutic approaches to anergy in surgical patients, Ann Surg 1979 September 190(3):286296.
[22]Faist E., Ertel W., Salmen B., Weiler A., Ressel C., Bolla K., Heberer G., The immune-enhancing effect of perioperative thymopentin administration in elderly patients undergoing major surgery, Arch Surg 1988 December 123:1449–1453.

DETAILED DESCRIPTION OF THE INVENTION

This invention describes a method of the use of dsRNA for the treatment of shock as identified by an impaired skin test or other mechanism. dsRNA may be administered in suitable dose and schedule as described below.

Below described is a typical experiment. Thirty male Sprague-Dawley rats (380–430 gms) were sensitized to keyhole limpet hemocyanin (KLH), 0.5 mg, in 0.1 ml complete Freund's adjuvant (DFA). Recall DTH skin testing was done two weeks later (Day 0). Skin test methodology for this purpose has been extensively documented by Tellado-Rodriguez and Christou (attached) and by Bates[23]. Other methods of determining immune dysfunction may be alternatively be used. Animals were divided into three groups. Group 1 (N=10) served as the control group. On day 1 all animals were anesthetized with Rompine 4 mg/kg and Ketamine 175 mg/kg intraperitoneally (IP) and in Groups 2 (N=10) and 3 (N=10), a dorsal full thickness 25% body surface area (BSA) immersion burn was created. All animals were resuscitated with 15 ml of normal saline IP. In Groups 2 and 3, 10(8) colony-forming units of Staphylococcus aureus were injected subcutaneously on days 1, 3, 7, and 13. Group 3 animals were given 15 mg/kg of dsRNA (Ampligen®) intravenously on days 1 through 5 through the tail vein. Recall skin testing with 0.25 mg KLH in 0.1 ml CFA was done on days 3, 7 and 13; the size of the skin response was measured with calipers. The animals were sacrificed in a carbon dioxide chamber on day 14.

[23]Bates, S. E., Suen J. Y., Tranum B. L., Immunological skin testing and interpretation; A plea for uniformity, Cancer 1979 June 43:2306–2314.

Average skin response in centimeters among each of the groups on days 3, 7 and 13 were compared using analysis of variance (ANOVA, FIG. 1)[24]. On days 3, 7 and 13 there was a significant difference in skin response between groups (p<0.0001, ANOVA); animals in Group 2 demonstrated a significant decrease from control. These results demonstrate that the immune response indicated by the depressed DTH response after a 25% BSA, thermal injury can be restored by intravenous injection of dsRNA during the first 5 days following injury (for graphical interpretations see FIG. 2 below). Two other test groups, a burn only group was similar to the burn+staphylococcus group and a low dose dsRNA (5 mg/kg) group was intermediate between the burn group and high dose dsRNA (15 mg/kg). This is indicative of a dose-dependent immune response to dsRNA.

[24]Karmy-Jones, R., Hinson D., Henriques H. F., Einck L., Fakhry S. M., DePalma R. G., Restoration of delayed hypersensitivity by an immune modulator following thermal injury, 1989 October Surgical Forum.

In experiments of this type, a high level of mortality is expected with a 25% full skin thickness thermal injury. As would be expected, two deaths occurred in the burn only group and three deaths occurred in the burn+staphylococcus group (for a graphical representation, see FIG. 3 below). However, only one death was observed in the low dose (5 mg/Kg) dsRNA group and no deaths were observed in both the unburned control and the high dose dsRNA group (15 mg/Kg). These data demonstrate that dsRNA generated a dose-related decrease in mortality due to restoration of immune function.

In addition to the restoration of cell-mediated immune function as demonstrated by skin testing and an improved prognosis, dsRNA elicited a profound change in macrophage activity. In a typical experiment, peritoneal macrophages from rats which had either received no treatment (control), a 25% body surface burn (burn only) or a 25% body surface burn and dsRNA administration by intravenous infusion on 5 consecutive days following thermal injury were collected 14 days after injury and tested for activity. It is well known that the function of macrophages is to engulf bacteria and other 'foreign' material which they encounter. We have utilized a test which mimics that activity and results in a accurate quantitative assessment of the activity level of the macrophages. The isolated macrophages are mixed with latex beads thereby challenging the macrophages to phagocytose or 'swallow' them. The proportion of macrophages that respond to the challenge is a quantitation of the level of activity of the macrophage component of the immune system. The number of latex beads which are inside the macrophages can readily be determined by fluorescent microscopy. In the following experiment, the macrophages from untreated rats are evenly divided between the three activity ranges; unresponsive (0 beads), moderately active (1–5 beads) and fully active (>5 beads)(see FIG. 4 for a graphic representation of macrophage activity). The burn injury itself causes a modest shift to increased activity as reflected by a decrease in unresponsive macrophages and increases in both moderately active and fully active cells. dsRNA treatment following the burn injury results in a dramatic shift of macrophage activity. Greater than 75% of the macrophages are fully active following exposure to dsRNA.

These experiments clearly demonstrate that application of dsRNA following thermal injury results in increased survival and restoration of immune function. The macrophage system and cell-mediated immune system may represent the primary defense mechanisms of a thermally injured patient against infection. Nearly all mortality in burn patients who survive resuscitation is caused by bacterial infection.

One lymphokine which has been shown to be responsible for enhancing macrophage activity is called tumor necrosis factor (TNF). Experiments to examine the possibility that dsRNA may elicit synthesis or release of TNF revealed that dsRNA does indeed result in increased levels of TNF in rats (see FIG. 5 below). A group of 4 rats were infused with dsRNA (15 mg/ml). Significant TNF levels[25] were induced in 2 of the animals in less that two hours.

[25]Meager A., Leung H., Wooley J., Review Article; Assays for tumour necrosis factor and related cytokines. J. Immuno Methods 1989 116:1–17.

However, induction of TNF, while it does correlate with increased macrophage and antiviral activity, is not in and of itself necessarily good. TNF levels are associated with the complications of septic shock[26]. Some researchers believe that the mortality associated with septic shock is a direct result of the release of TNF. This can be demonstrated by using an animal model which mimics the physiology of septic shock. Intravenous injection of purified lipopolysaccharide from gram negative bacteria (LPS) into rats (or other animals) results in symptomotology identical to septic shock and initiates the cascade of events which typically ends in death of the animal. In a classic experiment, infusion of antibodies to TNF prior to LPS infusion prevented the mortality associated with endotoxin[27]. The effectiveness of dsRNA for the symptomotology commonly associated with sepsis was tested as follows:

[26]Schirmer W. J., Schirmer J. M., Fry D. E., Recombinant Human Tumor Necrosis Factor produces hemodynamic changes characteristic of sepsis and endotoxemia, Arch Surg 1989 April 124:445–448.

[27]Beutler B., Milsark I. W., Cerami A. C., Passive immunization against cachectin/tumor necrosis factor protects mice from lethal effect of endotoxin, Science 1985, 229:869–871.

In a typical experiment, rats were infused with LPS (0.5 mg/kg). As expected, within 12 hours, 100% of the rats had died with symptomotology consistent with septic shock. Rats which had been treated with a single dsRNA (15 mg/kg) infusion 30 minutes prior to LPS infusion survived for greater than 36 hours. Approximately 50% of the dsRNA-treated animals were still alive after 48 hours and were sacrificed. In LPS injected rats, significant levels of TNF were induced (FIG. 6 following).

This induction correlated with septic shock symptomotology and death. Previous experiments of this type established that TNF is the lymphokine responsible for the observed mortality[28].

[28]Schirmer W. J., Schirmer J. M., Fry D. E., Recombinant Human Tumor Necrosis Factor produces hemodynamic changes characteristic of sepsis and endotoxemia, Arch Surg 1989 April 124:445–448.

Given the observations that the dsRNA-treated animals experienced increased survival, and the relationship between sepsis-related mortality and TNF, it was an extremely unexpected result that the rats which had been treated with dsRNA not only survived but expressed an equally dramatic TNF induction following LPS infusion. dsRNA provided protection of the animal from the toxic effects subsequent to LPS, or in a clinical setting, to sepsis.

Many mismatched dsRNA polymers which behave similarly to Ampligen have been studied. The rapid clearance of mismatched dsRNA from extracellular body fluids and hence the observed markedly decreased toxicity may be due to rapid degradation secondary to the presence of mismatches which allow ready access by nucleolytic enzymes.

The known activities of various interferons, interferon inducers and dsRNAs have been described (see the *Handbook of Experimental Pharmacology on Interferons*, edited by P. E. Came and W. A. Carter, 1984, published by Springer-Verlag, New York and Heidelberg; pages 535–555 describe some of the known properties of dsRNAs).

The present invention is based on another new and unexpected property of dsRNA, including but not limited to mismatched dsRNA, as exemplified by Ampligen.

The present invention provides for the use of dsRNA for the treatment of shock or injury.

An important symptom of the shock or injury is the suppression of the normal immune state as indicated by the immune skin response. This is restored during successful treatment with dsRNA.

Accordingly, the invention includes the use of dsRNA for restoring an anergic state to a substantially normal immune state as measured by testing the immune response.

The utility of the dsRNAs as cytokines or biological activators is well known[29]. A variety of dsRNAs have been examined and found to elicit similar biological effects. For example A. G. Johnson reviewed the immunomodulating properties of poly I:C and poly A:U and found them to be identical[30] Chapekar et al compared the cytocidal potentiation of a variety of dsRNAs (poly I:C, poly A:U, poly ICLC and rIn, $(C_{12}U)n$) and found them to be similar[31].

[29]Greene J. J., Ts'o POP, Double-stranded RNA and its analogs: The prospects and the promise of the first nucleic acid therapeutic agent, In: Clinical Applications of Interferons and Their Inducers, 2nd ed., Stringfellow D. A., ed., New York: Marcel Dekker, Inc., pp 245–268. Greene J. J., Ts'o POP, Strayer D. R., Carter W. A., Therapeutic applications of double-stranded RNAs, In: Interferons and Their Applications, Came P. E. and Carter W. A., eds., Berlin: Springer, 1984, pp 535–555.

[30]Johnson A. G., Immunomodulating effects of synthetic polyribonucleotides J Biol Resp Modif 4:481–3, 1985.

[31]Chapekar M. S., Glazer R. I., Potentiation of the cytocidal effect of human immune interferon by different synthetic double-stranded RNAs in the refractory human colon carcinoma cell line BE, Cancer Res 1986 April; 46(4 Pt 1):1698–702.

dsRNAs and analogs which have been used as therapeutic agents include poly I:C, poly ICLC, poly ICL-CM dextran, rIn, $(C_{12}U)n$ (i.e. Ampligen®), poly A:U, poly G:C and poly I:mercaptopolycytidylic acid.

The dsRNA may be a mismatched dsRNA. By "matched dsRNA" are meant those in which hydrogen bonding (base stacking) between the counterpart strands is relatively intact, i.e. is interrupted on average less than one base pair in every 29 consecutive base residues. The term "mis-matched dsRNA" should be understood accordingly.

The dsRNA may be a complex of a polyinosinate and a polycytidylate containing a proportion of uracil bases or guanidine bases, e.g. from 1 in 5 to 1 in 30 such bases (poly I,poly (C4–29×U or G).

The dsRNA may be of the general formula rIn, $(C_{12}U)n$. Other suitable examples of dsRNA are discussed below.

The mismatched dsRNAs may also be created by modifying adenosine residues in non-homopolymeric RNA to inosine such that inosine:uridine mismatches are created.

Pharmaceutical compositions in accordance with this invention include the dsRNA together with a pharmaceutically acceptable carrier or diluent. Pharmaceutical compositions contemplated by this invention include those adapted for parenteral administration in a suitable pharmaceutical vehicle.

Thus, for example, parenteral solutions, suspension and dispersions can be prepared as required according to known pharmaceutical techniques with sterile or pyrogen-free water as the diluent optionally also with physiologically acceptable salts.

As one of the significant receptors of dsRNA therapy, the use of micelles or liposomes to specifically target the drug to macrophages is appropriate in certain clinical situations to avoid generalized immune activation. As dsRNA in liposomes would go primarily to macrophages due to their phagocytic activity and would thereby not serve as a general immune activator, this delivery mechanism would be appropriate for immune modulation of the macrophage component of the immune system in organ transplantation patients whereby cell mediated immunity, and thereby organ rejection, is therapeutically repressed. However, targeted (liposome directed) dsRNA activation of the macrophage component of the immune system to provide protection from bacterial or viral infection while not stimulating cell-mediated immunity would be appropriate and beneficial.

It will be understood that the absolute quantity of active ingredients present in any dosage unit should not exceed that appropriate to the rate and manner of administration to be employed, but on the other hand should also desirably be adequate to allow the desired rate of administration to be achieved by a small number of doses. The rate of administration will moreover depend on the precise pharmacologic action desired.

The amount of dsRNA administered is preferably sufficient to achieve a level of from 0.01 micrograms per milliliter of body fluid after equilibrium of the dsRNA level through the body fluid up to 1000 micrograms per milliliter in the systemic circulation immediately following administration. As used herein, the term body fluid is the solution of blood, lymph, etc. which circulates within the organism and bathes the tissues. Expected body fluid volumes of patients are of course known to practitioners and are published as charts and tables, which are routinely available.

OBJECTS AND ADVANTAGES OF THE INVENTION

This invention describes a mechanism for the selective reactivation of natural defense systems within human cells, tissues and organs reduced to inadequate function subsequent to injury. As the immune system can be critical for survival during a period of great stress and challenge of infection, the therapy can improve the injured patient's prognosis.

LIMITED TO THE PARTICULAR FORMS(S) SHOWN)

dsRNA therapy as described in this invention is appropriate for shock subsequent to all manner of injury. These include, but are not limited to: trauma, burns, surgery, transfusion, radiation therapy and some chemotherapy. The rationale for the utility of dsRNA therapy for the immune depression associated with radiotherapy (i.e. radioprotection[32]) is described.

[32]Neta R., Role of cytokines in radioprotection, Pharmac. Ther. 1988 39:261–266.

I claim:

1. A method of treating septic shock comprising administering to a patient in need of same an effective amount of a dsRNA.

2. The method of claim 1 in which the dsRNA is poly (I):poly ($C_n$U) where n=12.

3. A method of treating septic shock subsequent to trauma, burns, surgery, transfusion, radiation therapy or chemotherapy comprising administering to a patient in need of same an effective amount of poly I:poly $C_{12}$U.

* * * * *